United States Patent [19]

Fisher et al.

[11] Patent Number: 5,466,441
[45] Date of Patent: Nov. 14, 1995

[54] NAIL POLISH DRYING METHOD

[76] Inventors: Frances E. Fisher; Joseph S. Fisher, 4502 Meager Cir., Port Charlotte, Fla. 33948

[21] Appl. No.: 265,255

[22] Filed: Jun. 29, 1994

[51] Int. Cl.[6] ........................................ A61K 7/04
[52] U.S. Cl. ............................... 424/61; 424/401
[58] Field of Search ............... 424/401, 61; 106/252, 106/264, 310

[56] References Cited

U.S. PATENT DOCUMENTS

| | | | |
|---|---|---|---|
| 4,301,048 | 11/1981 | Hirayama et al. | 260/22 CQ |
| 5,045,309 | 9/1991 | Dell'Aquila | 424/61 |
| 5,248,799 | 9/1993 | Schmutzler | 554/192 |
| 5,310,487 | 5/1994 | LaMonica | 210/651 |

*Primary Examiner*—Thurman K. Page
*Assistant Examiner*—Sharon Howard
*Attorney, Agent, or Firm*—Frank A. Lukasik

[57] ABSTRACT

A method for drying nail composition enamel in sixty seconds comprising the application of processed cotton seed oil to nail polish composition on natural and synthetic nails.

4 Claims, No Drawings

NAIL POLISH DRYING METHOD

BACKGROUND OF THE INVENTION

1. Field of the Invention

This invention relates generally to nail polish drying, and more specifically, to a novel method and product for drying nail polish in sixty seconds.

2. Discussion of the Prior Art

A large number of methods and compositions for beautifying and strengthening the nails of humans are well known. Prior art methods include coating the nail of an animal, including humans, with a composition including a film-forming polymer and additional ingredients such as pigment, plasticizer, and solvents, or alternatively, attaching preformed artificial nails to human nails with adhesives. Additional methods include adding cross linkable polymers to nail coating compositions to mend, strengthen and elongate natural nails and repairing nails with a fabric patch.

Most nail compositions presently on the market or disclosed in prior art, dry in five minutes or longer. Even those nail enamels that claim to be quick-dry, i.e., dry in about five minutes, are often not truly dry but rather are only dry to the touch. When a purportedly "dry" nail enamel of the prior art brushes up against a hard surface, the nail enamel often smudges, leaving tack.

One prior art composition for reducing the drying time is shown in U.S. Pat. No. 4,798,720 to Holder. The composition is a mixture of commercially available products, a top coat polish, an acrylic nail powder, an acrylic nail primer, and an adhesive. The top coat polish is a commercial product with a nitrocellulose base. In use, the new composition is applied as a base coat layer, a color polish is coated on top of the first layer, another layer of the new composition is applied over the color polish as a third layer, another coat of color polish is applied over the third layer, and another coat of the new composition is applied over the second color polish as the fifth layer. By using the five step coating sequence, drying times are reduced.

Another composition for reducing the drying time is U.S. Pat. No. 5,130,125 to Martin et al. The composition, for application over a nail polish, consists essentially of cellulose acetate butyrate resin, a mixture of solvents for dissolving the cellulose acetate butyrate resin to form a first solution, a plasticizer for the first solution, and a solvent for the plasticizer, providing a dry, non-tacky, non-brittle solid coat and which is quick drying when applied over a nail polish while wet.

U.S. Pat. No. 5,093,108 to Pappas et al comprises a primary film-forming polymer, a secondary film-forming polymer, at least one plasticizer, at least one thixotropic agent, at least one pigment, and an amount of acetone ranging from about 4.5% to about 35% by weight of said composition in combination with at least one additional solvent having sufficient polarity in combination with acetone to dissolve the primary and secondary film-forming polymers and said plasticizer to produce a stable composition.

U.S. Pat. No. 5,206,011 to Pappas et al discloses a quick-drying composition comprising sufficient quantities of organoclay thixotropic agents having acceptable static viscosities from about 400 to about 1200 centipoises and may accommodate numerous pigments to produce nail enamel compositions exhibiting favorable characteristics.

U.S. Pat. No. 5,275,807 to Pappas et al discloses a quick-drying composition comprising a primary film-forming polymer, a secondary film-forming polymer, e.g., a resin which functions to strengthen the primary film-forming polymer and improve the adhesion and gloss of the nail enamel, a plasticizer, and a solvent system containing a plurality of solvents one of which is acetone in an amount no less than about 4.5% and preferably no less than about 13% by weight of the product.

A composition which can be used to coat a natural or synthetic nail which dries in less than three minutes without requiring an additional application of a base coat or top coat would be very desirable. Nail polishes which dry in a period of less than 150 seconds would be even more desirable, as would polishes that dry in periods less than 90 seconds. A nail polish composition which would dry in a period of no greater than about 60 seconds would be especially useful in situations where "drying" time is important.

Working women need to have a product which can be easily applied and which dries in the shortest amount of time to avoid a situation where they are simply wasting precious time waiting for their nail polish to dry. In the manicure and pedicure industries, a colored nail polish composition which can dry in a period less than three minutes would provide a significant advantage over the prior art compositions.

Traditionally, when one performs a manicure or pedicure, after sufficiently cleaning and drying the nails, a layer of base coat nail polish is applied to the surface of the nail. The base coat polish is typically colorless. Thereafter, coats of colored nail polish are sequentially applied to the nails. Typically, up to three coats of colored polish are applied, and more typically, two coats are applied. Thereafter, a layer of top coat colorless nail polish is applied onto the colored nail polish. This sequence of base coat, colored polish, and top coat polish remains substantially the same, whether the nails are natural or acrylic.

Additionally, although the base coat/colored, polish/top coat, polish procedure is typically used, a long period of time is required for the colored polish to completely dry, typically from at least 15 to 30 minutes, and possibly longer.

Therefore, when an individual is in a hurry, such as a professional business woman, it is impossible to have an adequate amount of time for a manicure or pedicure. This can be particularly detrimental when the business woman is meeting a client or making a presentation and wants her nails to have a manicured look.

In addition, there exists a need for a product which is to be used in connection with colored nail polish to reduce the drying time of the colored polish. Further, there exists a need for reducing the number of chemicals used by cosmetologists when performing manicures.

OBJECTS OF THE INVENTION

It is therefore an object of the present invention to provide a nail drying product which can be applied to nail polish on natural and synthetic nails and will dry the nail polish in sixty seconds.

It is a further object of the present invention to provide a general method for applying a nail polish drying product to dry nail polish in sixty seconds after application.

These and other objects of the present invention may be readily determined from the detailed description of the invention which is set forth herein

DETAILED DESCRIPTION OF THE INVENTION

The present invention entails a new and novel use of cotton seed oil. The cotton seed oil of the present invention is refined, bleached and deodorized to a stage that is edible. Cotton seed oil is at present being used as a cooking oil and in the manufacture of margerine. The refining process is as follows: seeds from the cotton plant are pressed into a black, crude oil and the crude oil is then put through a refining process with Diatomaceous Earth and Flux Calcined. To prevent oxidative rancidity, the cotton seed oil is then processed with BHA, Propyl Gallate, Citric Acid and Propylene Glycol. The processed cotton seed oil is now a pale yellow, odorless, edible oil.

We have discovered that an application of the processed cotton seed oil, as described above, will dry a manicure of a base coat, two coats of nail polish, and a top coat in sixty seconds. The process of the present invention consists of waiting one minute after application of the enamel and top coat, and then brushing on a generous amount of the processed cotton seed oil of the present invention. In sixty seconds the nail enamel will be dry.

While not being limited by way of theory, it is believed that the processed cotton seed oil of the present invention is responsible for creating an interaction with the solvents utilized in the nail polish compositions currently available on the market, to substantially reduce the drying times of the nail polish compositions to sixty seconds.

It is obvious from a review of the specifications of the above cited references that the prior art nail polish drying compositions have used many types of volatile matter (solvents), such as for example, Ethyl alcohol, acetone, ethylene glycol monomethyl ether, and ethylene glycol monobutyl ether. In contrast, the present invention uses an edible cotton seed oil which is non-toxic, non-harmful to infants, biodegradable and easily disposable.

The invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

What is claimed is:

1. A rapid method of drying a nail polish composition on a nail which consists of:

a) applying on said nail a base coat, two coats of nail polish and a top coat;

b) waiting one minute after application of said nail polish and top coat;

c) brushing on said nail and over said nail polish and top coat, a processed cotton seed oil, wherein said processed cotton seed oil is produced by pressing said oil from cotton seeds, refining said oil with diatomaceous earth and flux calcined, and preventing rancidity by a treatment with a combination of BHA, propyl gallate, citric acid and propylene glycol.

2. The process of claim 1 wherein said nail is a natural nail.

3. The process of claim 1 wherein said nail is a synthetic nail.

4. The process of claim 1 wherein said nail polish composition is dried in sixty seconds.

\* \* \* \* \*